(12) United States Patent
Monassevitch

(10) Patent No.: US 6,517,556 B1
(45) Date of Patent: Feb. 11, 2003

(54) SHAPE MEMORY ALLOY CLIP AND METHOD OF USE THEREOF

(75) Inventor: Leonid Monassevitch, Givat Olga (IL)

(73) Assignee: NiTi Alloys Technologies Ltd., Netanya (IL)

( * ) Notice: Subject to any disclaimer, the term of this patent is extended or adjusted under 35 U.S.C. 154(b) by 271 days.

(21) Appl. No.: 09/697,441

(22) Filed: Oct. 26, 2000

(30) Foreign Application Priority Data

Oct. 28, 1999 (IL) .................................................. 132635

(51) Int. Cl.$^7$ .............................................. A61B 17/00
(52) U.S. Cl. ..................................... 606/151; 606/157
(58) Field of Search ................................ 606/151, 157, 606/158, 221, 153, 219; 24/543, 545, 556; 623/1.1, 1.11, 1.13, 1.15, 1.16, 1.18, 1.19, 1.34, 1.36

(56) References Cited

U.S. PATENT DOCUMENTS

| | | | |
|---|---|---|---|
| 3,774,615 A | * 11/1973 | Lim et al. | 606/151 |
| 3,974,835 A | * 8/1976 | Hardy, Jr. | 606/151 |
| 5,171,252 A | 12/1992 | Friedland | |
| 6,171,320 B1 | * 1/2001 | Monasseritch | 606/151 |
| 6,190,397 B1 | * 2/2001 | Spence et al. | 606/153 |

FOREIGN PATENT DOCUMENTS

| EP | 0 326 757 B1 | 7/1993 |
|---|---|---|
| SU | 1186199 A | 10/1985 |

* cited by examiner

Primary Examiner—Gloria M. Hale
(74) Attorney, Agent, or Firm—Pearne & Gordon LLP

(57) ABSTRACT

A surgical clip system which includes a surgical clip having a first clip portion including a first length of material having a closed geometrical shape having a first surface, the shape having a central axis therethrough and having a central opening therein; a pair of support portions associated with the first clip portion; a second clip portion including a second length of material having a closed geometrical shape having a second surface of substantially the same configuration and size as that of the first clip portion, the shape having a central axis therethrough; and a pair of fastening elements formed of a shape memory alloy, each of the fastening elements including a first end and a second end, each of the first ends being attached to the second clip portion; wherein, when at a first temperature or higher, the shape memory alloy is in an elastic state, such that the pair of fastening elements are maintained in a position such that they abut the support portions, and wherein, when at a second temperature or lower, below the first temperature, the shape memory alloy is in a plastic state, thereby enabling the second ends of the pair of fastening elements to be moved away from the second length of material and to be passed between the support portions such that, upon heating of the clip to at least the first temperature, the pair of fastening elements returns to the position such that they abut the support portions, thereby pressing against the pair of support portions, thereby pressing the first and second lengths of material towards each other, thereby to apply a compressive force to tissue located between the first and second lengths of material.

45 Claims, 11 Drawing Sheets

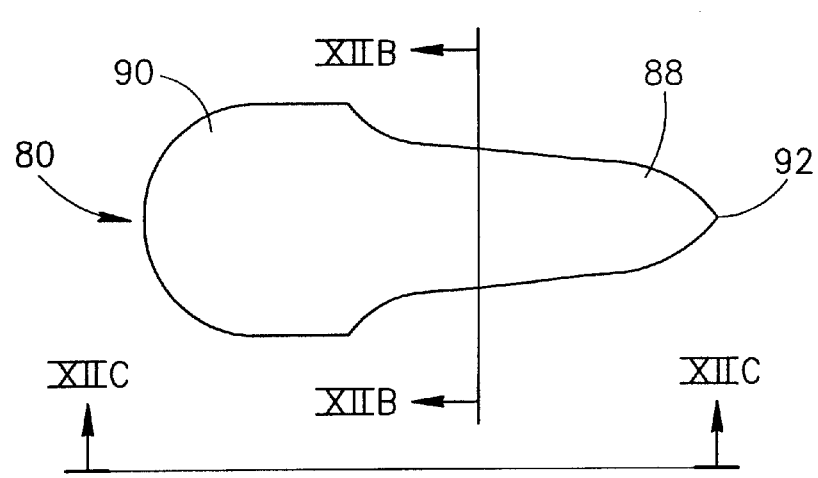
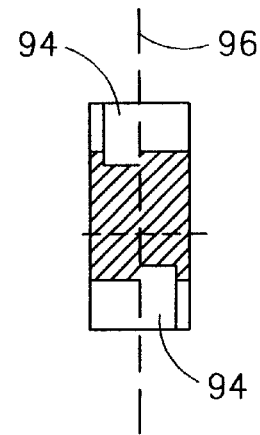
FIG.12A  FIG.12B
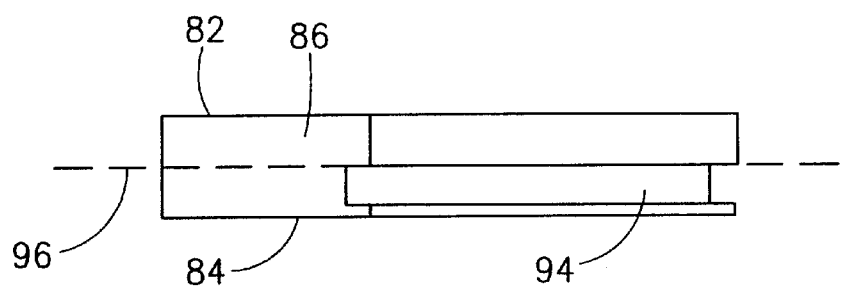
FIG.12C

SHAPE MEMORY ALLOY CLIP AND METHOD OF USE THEREOF

FIELD OF THE INVENTION

The present invention relates, generally, to the field of surgical clips and, in particular, to the field of surgical clips including a shape memory alloy (SMA).

BACKGROUND OF THE INVENTION

Several methods are known in the art for joining portions of hollow organs, such as those of the gastrointestinal tract. These include threads for manual suturing, staplers for mechanical suturing, and compression rings and clips.

While manual suturing is universally known and relatively inexpensive, the degree of success depends considerably on the skill of the surgeon. Another disadvantage is that post-operative complications are common. Further, suturing an organ results in lack of smoothness of the tissue therein, which hampers peristalsis in the sutured area. Finally, suturing is both labor and time consuming.

Staplers for mechanical suturing ensure a reliable joining of tissue and enable the time needed for surgery to be reduced, compared with manual suturing. However, due to the facts that such staples are not reusable and that a great many types and sizes are required, the price of staples is high. Also, after healing, metal staples remain in place along the perimeter of the suture, which reduces elasticity of the junction and adversely affects peristalsis.

Junctions using compression devices such as rings and clips ensure high quality seal and post-operative functioning of the organs. Two types of compression devices are known, namely, rings made of resorption plastics and clips made of shape memory alloys. Plastic rings are cumbersome and expensive. Also, the compression force is applied only momentarily at the junction and is reduced as the tissue is crushed. Clips made of shape memory alloys enable portions of tissue to be pressed together with increasing pressure and to provide constant pressure at body temperature, due to the inherent properties of the alloys.

Advantages of clips made of shape memory alloy materials include simplicity of design, low cost of manufacture, and smallness in size. Also, they possess universal qualities and they ensure their self-evacuation from the gastrointestinal tract.

It is known in the art to provide a surgical fastening clip which applies a clamping force to a site, such as a blood vessel, thereby reducing its cross-sectional area. It is also known to provide a surgical fastening clip formed of a shape memory alloy which deforms to a closed configuration when heated, such that the clamping force applied thereby is increased as it is heated. For example, U.S. Pat. No. 5,171,252 discloses a surgical fastening clip formed of a shape memory alloy, the device including separate legs which close tightly around a site. Such a device is limited in its uses, such as for clamping blood vessels, and is not suitable for joining portions of the gastrointestinal tract.

EP 0,326,757 discloses a device for providing anastomosis to a portion of a digestive tract, including a plurality of U-shaped retaining clips disposed around a soluble support tube. The tube is positioned inside portions of the digestive tract to be joined, and includes an outer groove around which are disposed the U-shaped retaining clips. The retaining clips are made of a shape memory alloy such that the open ends thereof close at a predetermined temperature, thus joining ends of the digestive tract. Once the ends of the digestive tract have been joined, the tube is dissolved. Such a device is disadvantageous in that a plurality of clips are required to be properly positioned simultaneously. Also, there is no assurance that the resulting junction will be smooth, due to the plurality of sites of the digestive tract joined by the plurality of clips.

SU 1,186,199 discloses a shape memory alloy clip consisting of two parallel coils which is used for joining portions of a hollow organ, such as an organ of the gastrointestinal tract. The portions of the organ to be joined are aligned and each of the coils is introduced through a puncture formed in the wall of one of the portions. The coils are positioned such that, when heated, they compress the aligned walls therebetween, thus maintaining the portions of the walls held within the loops of the coils adjacent each other. Thereafter, incisions are made through the portions of the walls held within the loops of the coils, such that a passageway is created between the two organ portions. The punctures in the organ walls must then be surgically sewn closed with interrupted surgical sutures.

A major disadvantage of this sort of shape memory alloy clips is that they permit compression of only approximately 80–85% of the junction perimeter, thus requiring additional manual sutures which reduce the seal of the junction during the healing period and its elasticity in the post-operative period. Furthermore, this additional suturing is problematic in as much as it has to be carried out across a join which includes a portion of the clip, thereby rendering difficult sealing and anastomosis of the organ portions.

SUMMARY OF THE INVENTION

The present invention seeks to provide an improved surgical clip system including a shape memory alloy, and a method of joining two portions of a hollow organ, which overcome disadvantages of prior art.

There is thus provided, in accordance with a preferred embodiment of the present invention, a surgical clip system which includes a surgical clip having a first clip portion including a first length of material having a closed geometrical shape having a first surface, the shape having a central axis therethrough and having a central opening therein; a pair of support portions associated with the first clip portion; a second clip portion including a second length of material having a closed geometrical shape having a second surface of substantially the same configuration and size as that of the first clip portion, the shape having a central axis therethrough; and a pair of fastening elements formed of a shape memory alloy, each of the fastening elements including a first end and a second end, each of the first ends being attached to the second clip portion; wherein, when at a first temperature or higher, the shape memory alloy is in an elastic state, such that the pair of fastening elements are maintained in a position such that they abut the support portions, and wherein, when at a second temperature or lower, below the first temperature, the shape memory alloy is in a plastic state, thereby enabling the second ends of the pair of fastening elements to be moved away from the second length of material and to be passed between the support portions such that, upon heating of the clip to at least the first temperature, the pair of fastening elements returns to the position such that they abut the support portions, thereby pressing against the pair of support portions, thereby pressing the first and second lengths of material towards each other, thereby to apply a compressive force to tissue located between the first and second lengths of material.

Additionally in accordance with a preferred embodiment of the present invention, the first clip portion, the support portions, and the second clip portion are fabricated from biocompatible material.

Further in accordance with a preferred embodiment of the present invention, each of the pair of support portions includes a pair of guide elements between which one of the fastening elements is positioned when in the elastic state and when the first and second lengths of material are pressed towards each other.

Yet further in accordance with a preferred embodiment of the present invention, the guide elements are fabricated from biocompatible material.

Still further in accordance with a preferred embodiment of the present invention, upon heating of the clip to at least the first temperature, the pair of fastening elements press against the pair of support portions, thereby pressing the first and second lengths of material towards each other such that they are maintained a distance apart of approximately 0.1–1.5 mm.

In accordance with another embodiment of the present invention, upon heating of the clip to at least the first temperature, the pair of fastening elements press against the pair of support portions, thereby pressing the first and second lengths of material against each other such that the first and second surfaces substantially abut each other.

In accordance with the present invention, the system further includes spacer means for facilitating movement of the second ends of the fastening elements away from the second length of material. The spacer means includes means insertable through the second length of material of the second clip portion. The insertable means includes means for guiding movement of the fastening elements away from the second length of material. The spacer means is fabricated from biocompatible material.

In accordance with a second embodiment of the present invention, there is provided a surgical clip system which includes a surgical clip having: a first clip portion including a first length of material having a closed geometrical shape having a first surface, the shape having a central axis therethrough and having a central opening therein; a pair of support portions associated with the first clip portion; a second clip portion including a second length of material having a closed geometrical shape having a second surface of substantially the same configuration and size as that of the first clip portion, the shape having a central axis therethrough; and a pair of fastening elements formed of a superelastic material, each of the fastening elements including a first end and a second end, each of the first ends being attached to the second clip portion; wherein, in the absence of an outside force, the pair of fastening elements are maintained in a position such that they abut the support portions, and wherein, by the application of an outside force, the second ends of the pair of fastening elements are movable away from the second length of material such that they may be passed between the support portions such that, upon removal of the outside force, the pair of fastening elements returns to the position such that they abut the support portions, thereby pressing thereagainst, thereby pressing the first and second lengths of material towards each other, thereby to apply a compressive force to tissue located between the first and second lengths of material.

In accordance with a preferred embodiment of the present invention, there is provided a method for anastomosing an organ of a gastrointestinal tract, the method comprising the following steps: (a) providing a surgical clip system which includes a surgical clip having: a first clip portion including a first length of material having a closed geometrical shape having a first surface, the shape having a central axis therethrough and having a central opening therein; a pair of support portions associated with the first clip portion; a second clip portion including a second length of material having a closed geometrical shape having a second surface of substantially the same configuration and size as that of the first clip portion, the shape having a central axis therethrough; and a pair of fastening elements formed of a shape memory alloy, each of the fastening elements including a first end and a second end, each of the first ends being attached to the second clip portion; wherein, when at a first temperature or higher, the shape memory alloy is in an elastic state, such that the pair of fastening elements are maintained in a position such that they abut the support portions, and wherein, when at a second temperature or lower, below the first temperature, the shape memory alloy is in a plastic state, thereby enabling the second ends of the pair of fastening elements to be moved away from the second length of material and to be passed between the support portions such that, upon heating of the clip to at least the first temperature, the pair of fastening elements returns to the position such that they abut the support portions, thereby pressing thereagainst, thereby pressing the first and second lengths of material towards each other, thereby to apply a compressive force to tissue located between the first and second lengths of material; (b) cooling at least the fastening elements of the clip to a temperature below its lower phase transition temperature; (c) moving the second ends of the fastening elements away from the second length of material; (d) preparing open ends of first and second organ portions to be joined, such that a cross-sectional area of each organ portion is narrowed relative to the remainder of thereof; (e) inserting the first clip portion into the first organ portion, such that the first length of material abuts the inside surface of the tissue thereof, adjacent the narrowed area thereof; (f) inserting the second clip portion into the second organ portion, such that the second length of material abuts the inside surface of the tissue thereof, adjacent the narrowed area thereof and such that the fastening elements protrude out of the open end of the second organ portion; (g) drawing together the open ends of the first and second organ portions wherein anastomosis is desired such that they face each other, and bringing the open ends closer together such that the fastening elements protruding out of the open end of the second organ portion pass into the open end of the first organ portion, through the first length of material, and through the pair of support portions; (h) maintaining the relative positions of the first and second portions of the gastrointestinal tract and the first and second clip portions in relation thereto, while raising the temperature of at least the fastening elements to a temperature above its upper phase transition temperature, such that the elasticity thereof causes the fastening elements to return to a position such that the fastening elements press against the pair of support portions, thereby pressing the first and second lengths of material towards each other, thereby to apply a compressive force to tissue located between the first and second lengths of material.

Additionally in accordance with the preferred embodiment of the present invention, in the step (h), the temperature of at least the fastening elements is raised to a temperature above its upper phase transition temperature by the artificial application of heat.

Further in accordance with the preferred embodiment of the present invention, the surgical clip system further includes spacer means for facilitating movement of the second ends of the fastening elements away from the second length of material; and, between steps (e) and (f), the method includes the additional step (e1) of: inserting the spacer means into the second organ portion. Between steps (f) and (g), the method includes the additional step (f1) of inserting the spacer means through the second length of material of the second clip portion, the fastening elements guided away from the second length of material. The spacer means is fabricated from biocompatible material.

In accordance with a second embodiment of the present invention, there is provided a method for anastomosing an organ of a gastrointestinal tract, the method comprising the following steps: (a) providing a surgical clip system which includes a surgical clip having: a first clip portion including a first length of material having a closed geometrical shape having a first surface, the shape having a central axis therethrough and having a central opening therein; a pair of support portions associated with the first clip portion; a second clip portion including a second length of material having a closed geometrical shape having a second surface of substantially the same configuration and size as that of the first clip portion, the shape having a central axis therethrough; and a pair of fastening elements formed of a thermoresilient material, each of the fastening elements including a first end and a second end, each of the first ends being attached to the second clip portion; wherein, in the absence of an outside force, the pair of fastening elements are maintained in a position such that they abut the support portions and wherein, by the application of an outside force, the second ends of the pair of fastening elements are moved away from the second length of material such that they are able to be passed between the support portions such that, upon removal of the outside force, the pair of fastening elements returns to the position such that they abut the support portions, thereby pressing, thereby pressing the first and second lengths of material towards each other, thereby to apply a compressive force to tissue located between the first and second lengths of material; (b) moving the second ends of the fastening elements away from the second length of material; (c) preparing open ends of first and second organ portions to be joined, such that a cross-sectional area of each organ portion is narrowed relative to the remainder of thereof; (d) inserting the first clip portion into the first organ portion, such that the first length of material abuts the inside surface of the tissue thereof, adjacent the narrowed area thereof; (e) inserting the second clip portion into the second organ portion, such that the second length of material abuts the inside surface of the tissue thereof, adjacent the narrowed area thereof and such that the fastening elements protrude out of the open end of the second organ portion; (f) drawing together the open ends of the first and second organ portions wherein anastomosis is desired such that they face each other, and bringing the open ends closer together such that the fastening elements protruding out of the open end of the second organ portion pass into the open end of the first organ portion, through the first length of material, and through the pair of support portions; (g) maintaining the relative positions of the first and second portions of the gastrointestinal tract and the first and second clip portions in relation thereto, while removing the outside force, thereby allowing the fastening elements to return to a position such that the fastening elements press against the pair of support portions, thereby pressing the first and second lengths of material towards each other, thereby to apply a compressive force to tissue located between the first and second lengths of material.

BRIEF DESCRIPTION OF THE DRAWINGS

The present invention will be more fully understood and appreciated from the following detailed description, taken in conjunction with the drawings, in which:

FIG. 12A is a schematic illustration of a surgical clip spacer, constructed in accordance with the present invention;

FIG. 12B is a cross-sectional view of the surgical clip spacer of FIG. 12A, taken in the direction of line XIIB—XIIB therein;

FIG. 12C is a side view of the surgical clip spacer of FIG. 12A, taken in the direction of line XIIC—XIIC therein;

DETAILED DESCRIPTION OF THE INVENTION

The present invention provides a surgical clip system including a surgical clip formed at least partly of a shape memory alloy, such as known in the art, and a method of use thereof, which provides organ tissue compression along the entire periphery of the clip, thereby to ensure satisfactory joining or anastomosis of a punctured organ.

Figure 1A:
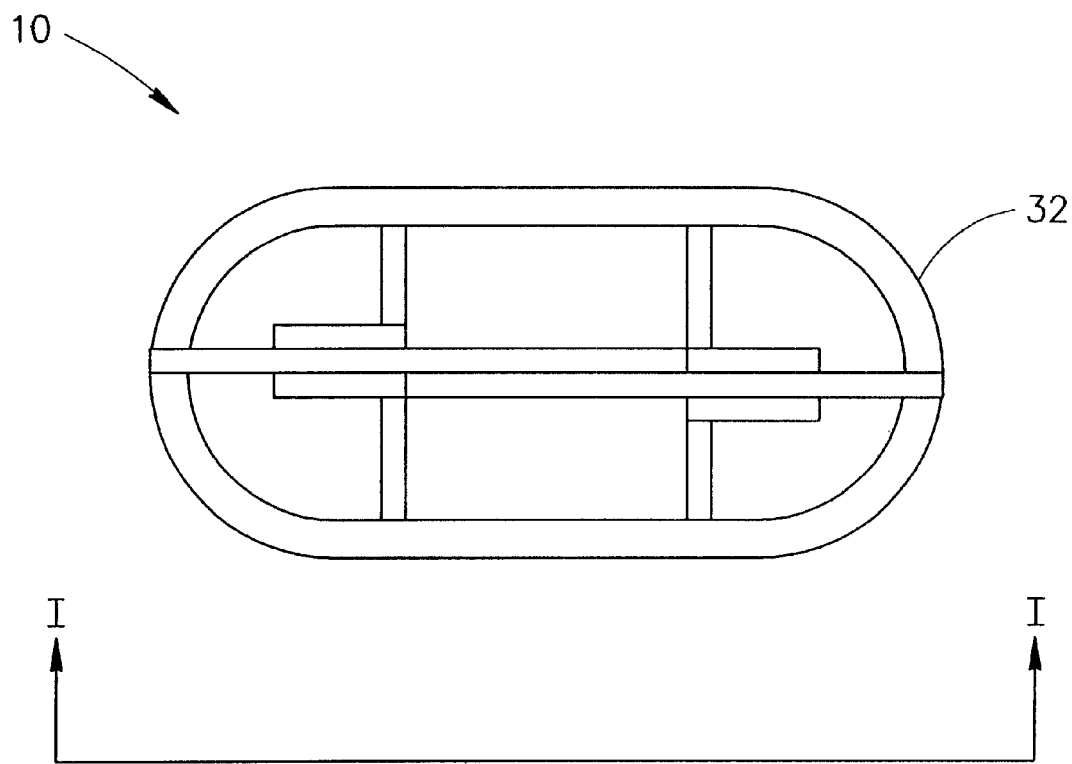
FIG. 1A is a pictorial illustration of a surgical clip, constructed in accordance with a preferred embodiment of the present invention.
Figure 1B:
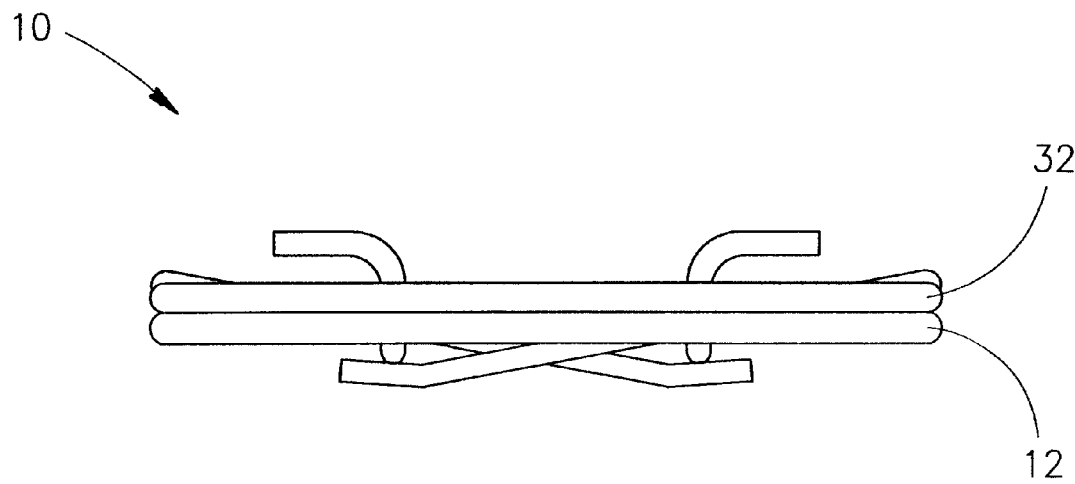
FIG. 1B is a side view of the surgical clip of FIG. 1A, taken in the direction of line I—I therein.
Figure 2A:
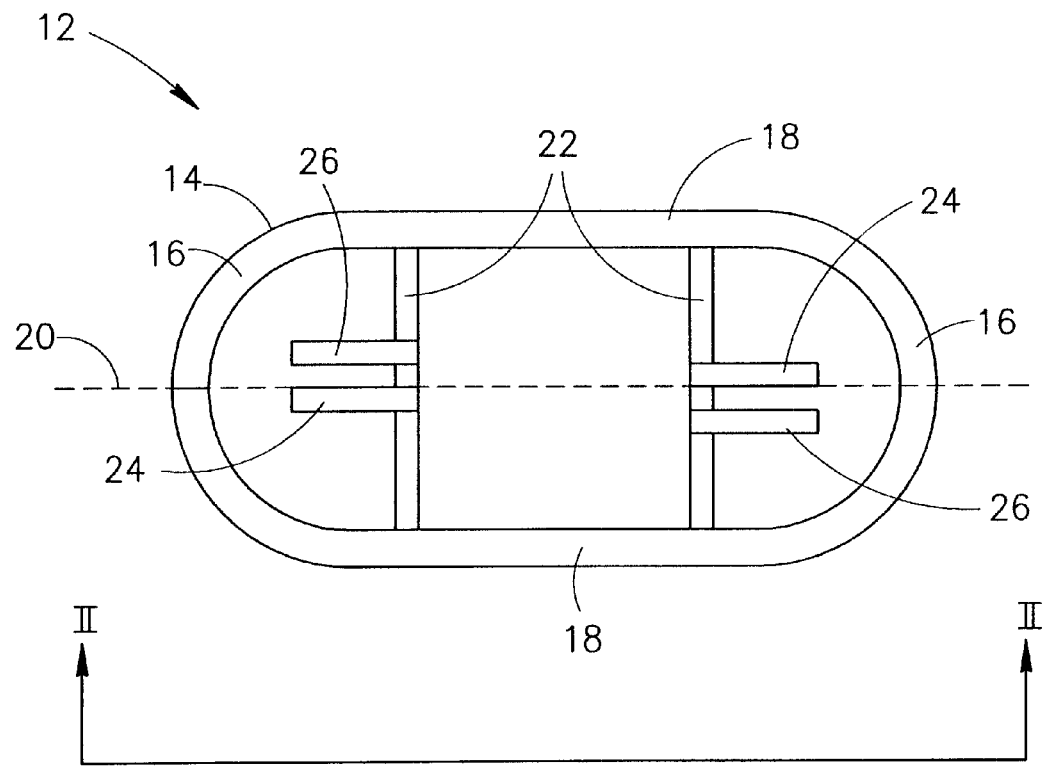
FIG. 2A is a pictorial illustration of a first element of the surgical clip of FIGS. 1A and 1B.
Figure 2B:
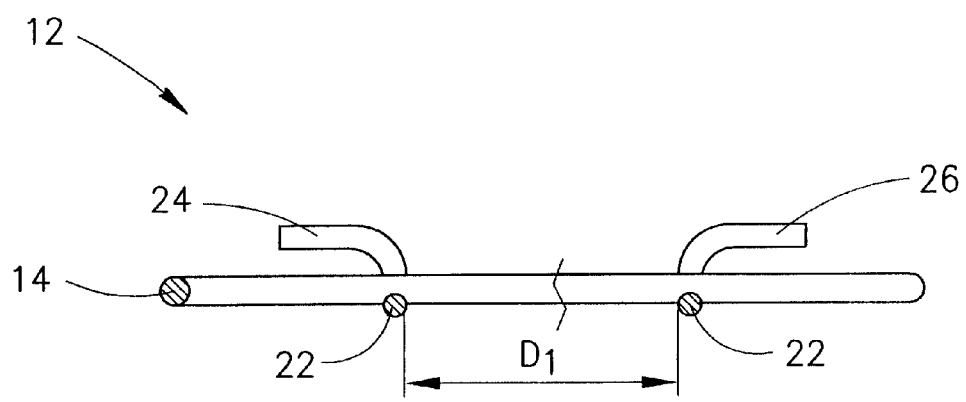
FIG. 2B is a side view of the first element of the surgical clip shown in FIG. 2A, taken along the line II—II therein.

Referring now to the drawings, FIGS. 1A and 1B illustrate a surgical clip, referenced generally 10, according to a preferred embodiment of the present invention. The clip 10 includes a first element 12 and a second element 32 which are to be fastened together, as will be discussed below. The features of first portion 12 are shown more clearly in FIGS. 2A and 2B, and the features of second portion 32 are shown more clearly in FIGS. 3A and 3B. First element 12 and second element 32 may be of any size and shape suitable for use in joining together organ portions, and their specific size and shape are to be determined by the size and shape of the organ portions to be joined.

First element 12 comprises a closed ring 14 having an axis of symmetry 20 which passes through end portions 16 of ring 14 and which passes between side portions 18 of ring 14. A pair of parallel, transverse support bars 22 is attached to side portions 18 of ring portion 14, the support bars 22 separated by a distance $D_1$. Each support bar 22 is preferably provided with a pair of spaced apart guide bars 24 and 26, disposed on either side of axis 20, such that guide bars 24 abut axis 20 on opposite sides thereof. While guide bars 24 and 26 are shown (FIGS. 1B and 2B) as being curved, it will be appreciated by persons skilled in the art that guide bars having any other configuration, such as straight bars, may be utilized, without affecting use of the clip 10. First element 12 may be fabricated from any metal or plastic material which is suitable for use in surgical procedures, such as plastic, stainless steel, or any other biocompatible material.

Second portion 32 (FIGS. 1A, 3A, 3B) includes a closed ring 34 having an axis of symmetry 30, which passes through end portions 36 of ring 34 and which passes between side portions 38 of ring 34. A pair of clamping bars 40 is attached to end portions 36, on either side of and parallel to axis 30. Ring 34 may be fabricated from any metal or plastic material which is suitable for use in surgical procedures, such as plastic, stainless steel, or any other biocompatible material, while clamping bars 40 are fabricated from a shape memory alloy or superelastic material, such as is known in the art, which is suitable for use in surgical procedures. If desired, only the actual joint of clamping bars 40 to ring 34 may be formed of a shape memory alloy/superelastic material, while clamping bars 40 may be made from any suitable metal or plastic material.

When first element 12 and second element 32 of clip 10 are properly fastened together, clamping bars 40 of second element 32 pass through support bars 22 of first element 12 and press thereagainst, so as to force rings 14 and 34 to abut one another along their entire circumference. The purpose of the guide bars 24 and 26 is to provide a means for the exact positioning of the clamping bars 40 relative to each other.

While the surgical clip 10 according to the present invention has been shown and described as one specific embodiment, it will be appreciated by persons skilled in the art that other configurations of the clip may be achieved without departing from the scope of the invention. For example, while rings 14 and 34 are shown in the drawings as being flat and oval and as having circular cross-section, other configurations of rings may be suitable for use in providing surgical clips according to the present invention, such as non-flat or circular clips or clips having non-circular cross-sections.

Figure 3A:
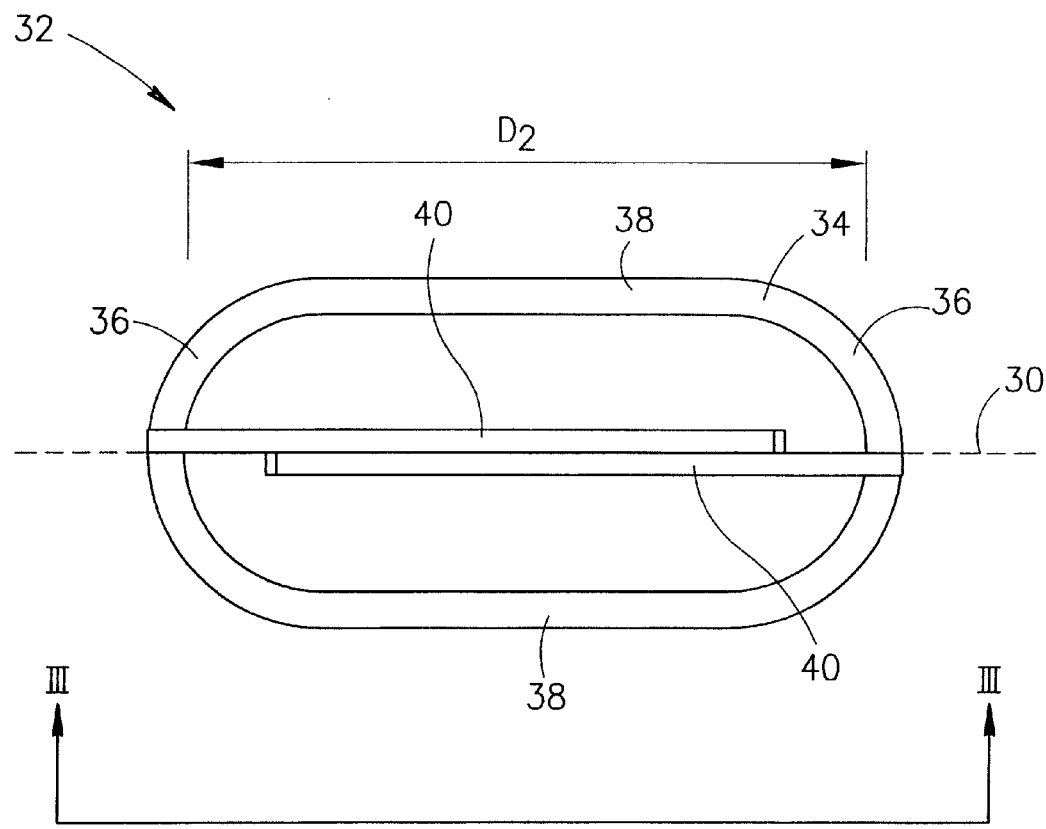
FIG. 3A is a pictorial illustration of a second element of the surgical clip of FIGS. 1A and 1B.
Figure 3B:
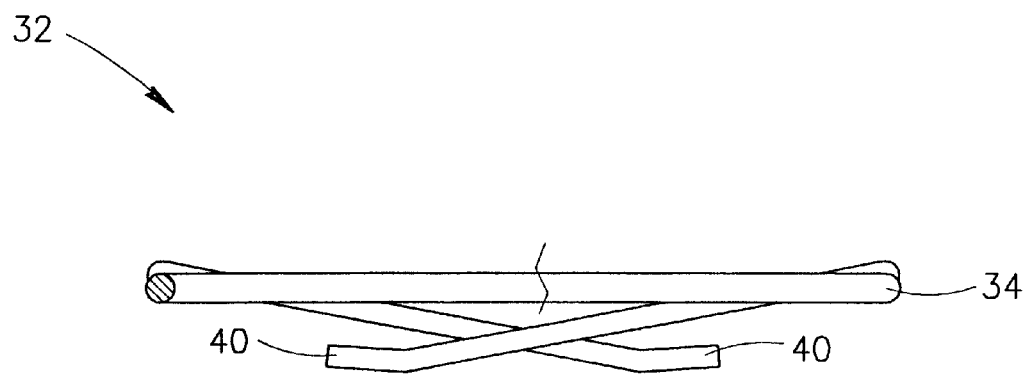
FIG. 3B is a side view of the second element of the surgical clip shown in FIG. 3A, taken along line III—III therein.

While clamping bars 40 shown in FIGS. 1A and 3A are configured so as to abut each other, it will be appreciated by persons skilled in the art that the amount of spacing between clamping bars 40 is to be determined by the relative distance between the guide bars 24 and 26 provided in first element 12 such that, when first element 12 and second element 32 are fastened together, as will be discussed below, each clamping bar 40 rests in its proper position between a pair of guide bars 24 and 26. Also, clamping bars 40 may either be configured as straight (not shown), curved as shown in FIG. 3B, or curved as shown in FIGS. 4 and 5.

The ring 14, support bars 22, guide bars 24 and 26 of first element may be attached by any means known in the art, such as by welding. Similarly, the ring 34 and clamping bars 40 of second element may be attached by any means known in the art, such as by welding. It will be appreciated by persons skilled in the art that the description of the present invention as shown in FIGS. 1–5 relates to a first embodiment of the present invention only, which is fabricated entirely of metal, and wherein the joins between any two portions are metal to metal joins. As will be discussed below with reference to FIGS. 6–10, if desired, the surgical clip of the present invention may be fabricated from both plastic and metal materials.

Figure 4:
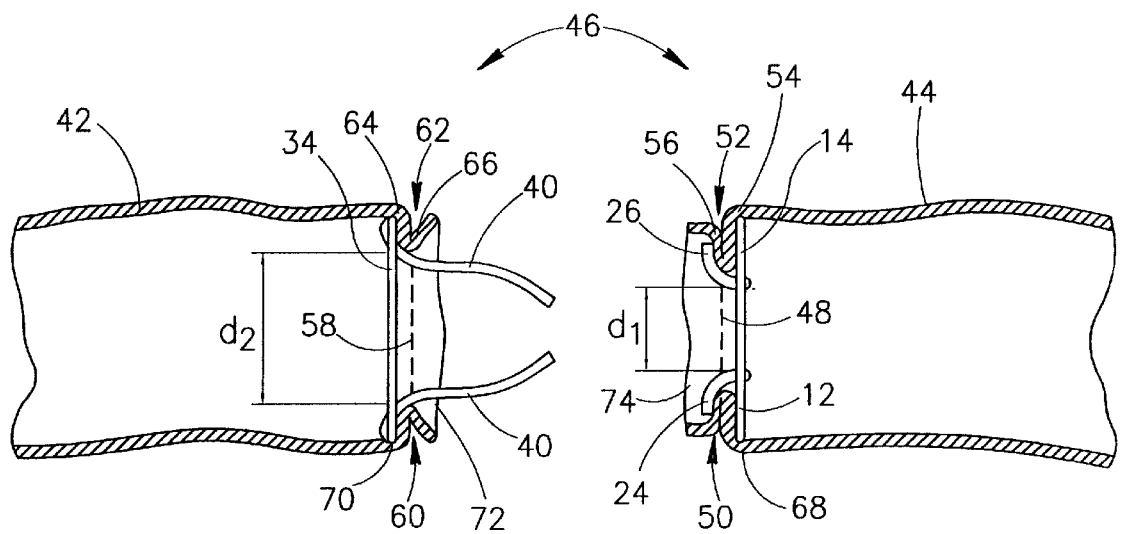
FIG. 4 is a pictorial cross-sectional illustration of first and second portions of a hollow organ, inside which there have been placed respective first surgical clip element, shown in FIGS. 2A and 2B, and second surgical clip element, shown in FIGS. 3A and 3B, in accordance with the first embodiment of the present invention, portions of the second element of the surgical clip being in a plastic state.
Figure 5:
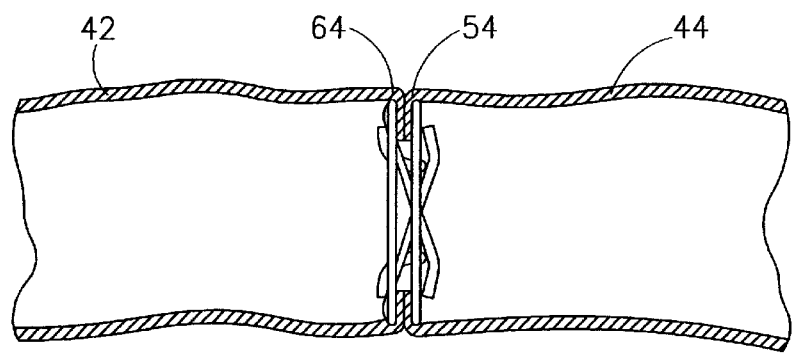
FIG. 5 is a cross-sectional view of the joined hollow organ portions shown in FIG. 4, with the surgical clip elements fastened together.

With additional reference to FIG. 4, there are shown portions 44 and 42, respectively, of a hollow organ 46, to which it is desired to provide anastomosis, as shown in FIG. 5. Organ portions 44 and 42 have respective open ends 74 and 72. The method of the present invention will now be described with reference to clip 10. However, it will be appreciated by persons skilled in the art that the method of the present invention may be carried out by utilizing any embodiment of the clip in accordance with the present invention.

A line of stitches 48, such as a line of purse string stitches, which are commonly used in surgical procedures, is surgically placed in a tissue section 50 located near the end of organ portion 44, along the periphery thereof, such that the stitches 48 pass therethrough. The stitches 48 are then gathered, by means known in the art, such that, at the location of the gathered stitches 48, the diameter $d_1$ of the cross-sectional area of organ portion 44 is reduced until it is approximately equals the distance $D_1$ (FIG. 2B) between support bars 22. First element 12 of clip 10 is then placed, via open end 74, inside organ portion 44, such that ring 14 is positioned along the inner surface thereof, and each of guide bars 24 and 26 is inserted between one of stitches 48 and the inner surface of tissue section 50. Insertion of the guide bars 24 and 26 will cause the tissue portions 54 and 56 to form a fold 52 along stitches 48, such that tissue portion 54 abuts ring 14 along its entire periphery. Organ portion 44 is then ready to be joined to organ portion 42.

As discussed above, clamping bars 40 of second element 32 of clip 10 may be fabricated either from a thermosensitive shape memory alloy or from a superelastic material. When employing a shape memory alloy, second element 32 is cooled until it reaches its lower phase transition temperature, as known in the art, the clamping bars 40 of second element 32 thus being in a plastic state. The phase transition temperature may be generally any temperature above −273° C., preferably in the range of 25–35° C., and below body temperature. Clamping bars 40 are moved apart a desired distance and second element 32 is preserved in the cooled state for as long as required until insertion into the organ portion 42. When employing a superelastic material, clamping bars 40 are moved apart a desired distance, by the use of a special instrument intended for this purpose, as discussed below.

A line of stitches 58 is surgically placed in a tissue section 60 located near the end of organ portion 42, along the periphery thereof, such that stitches 58 pass therethrough. The stitches are then gathered, by means known in the art, such that, at the location of the gathered stitches 58, the diameter $d_2$ of the cross-sectional area of organ portion 42 is reduced until it is less than the distance $D_2$ (FIG. 3A) between the side portions 38 of ring 34. Second element 32 of clip 10 is then placed, via open end 72, inside organ portion 42 such that ring 34 is positioned along the inner surface thereof, and each of clamping bars 40 is inserted between one of stitches 58 and the inner surface of tissue section 60, such that clamping bars 40 protrude out of the open end 72 of organ portion 42. Insertion of the clamping bars 40 will cause the tissue portions 64 and 66 to form a fold 62 along stitches 58, such that tissue portion 64 abuts ring 34 along its entire periphery.

As shown in FIG. 4, organ portions 42 and 44 of organ 46 are positioned adjacent one another, and are brought closer together, such that clamping bars 40 of second element 32 are inserted between support bars 22 of first element 12. Once they have been brought into contact, as shown in FIG. 5, tissue portion 64 of organ portion 42 abuts tissue portion 54 of organ portion 44. Clamping bars 40 are then allowed to return to their original position, relative to ring 34, either by warming of the second element by the organ portion 42, when a thermosensitive shape memory alloy is utilized, or by removal of the special instrument, when a superelastic material is used, as discussed above.

When employing a thermosensitive shape memory alloy, the relative positions of organ portions 42 and 44 of organ 46 and the relative positions of first element 12 and second element 32 in relation thereto must be maintained for a period of time during which the temperature of organ 46 is effective to cause the temperature of the clamping bars 40 to rise to at least its upper phase transition temperature, which, preferably, is body temperature. During the time that the temperature of clamping bars 40 rises towards its transition temperature, rings 14 and 34 converge and press tissue portions 54 and 64 of organ portions 44 and 42 located therebetween more and more tightly against each other. The rate by which the temperature of clamping bars 40 rises may be accelerated by heating clip 10, for example, by any method known in the art. Once the temperature of clamping bars 40 has risen above the transition temperature, clamping bars 40 have returned to their elastic state, as shown in FIGS. 1A, 1B, 3A, 3B, and 5, and maintain tissue portions 54 and 64 adjacent one another.

Due to the pressure exerted by clip 10 on organ portions 44 and 42, respective tissue portions 54 and 64 are pressed so tightly against each other that blood flow to these tissue portions ceases, resulting in eventual necrosis of these tissue portions 54 and 64. As tissue portions 54 and 64 die, the tissue portions 68 and 70 immediately thereoutside mend together such that portions 42 and 44 of organ 46 are joined and organ 46 may function as one continuous organ. Once tissue portions 54 and 64 die, they, together tissue portions 56 and 66 and with clip 10, become separated from organ portions 42 and 44, and are passed out of organ 46, by the normal activity thereof. For example, if organ 46 is the small intestine, and the direction of peristalsis is from portion 42 towards portion 44, then clip 10 and tissue portions 54, 64, 56, and 66 will be passed through portion 44 by the normal activity of the small intestine.

Figure 6A:
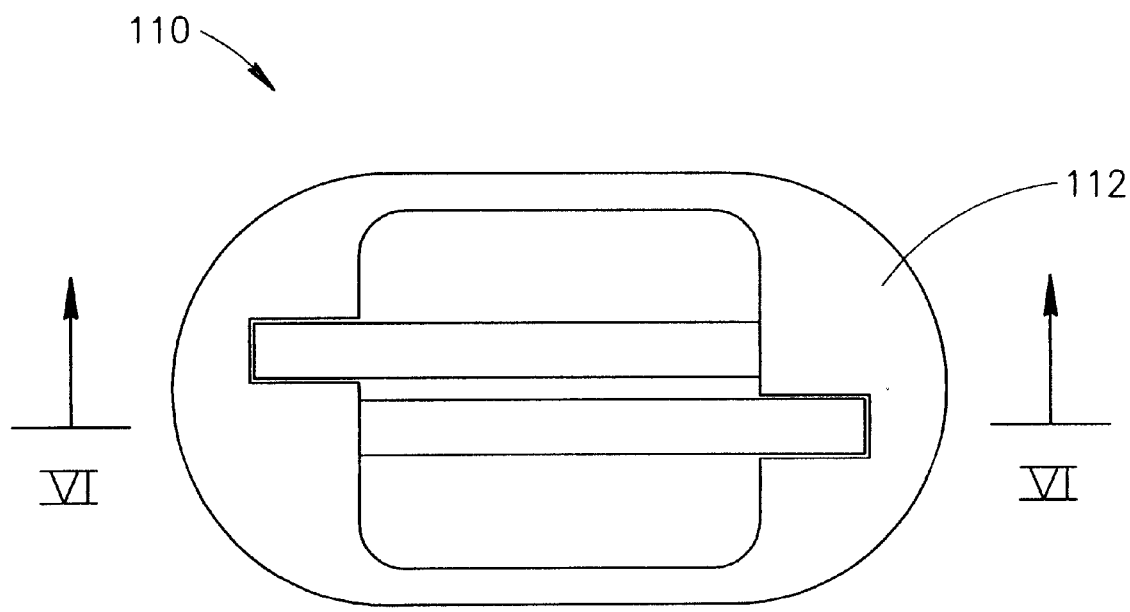
FIG. 6A is a pictorial illustration of a surgical clip, constructed in accordance with a second embodiment of the present invention.
Figure 6B:
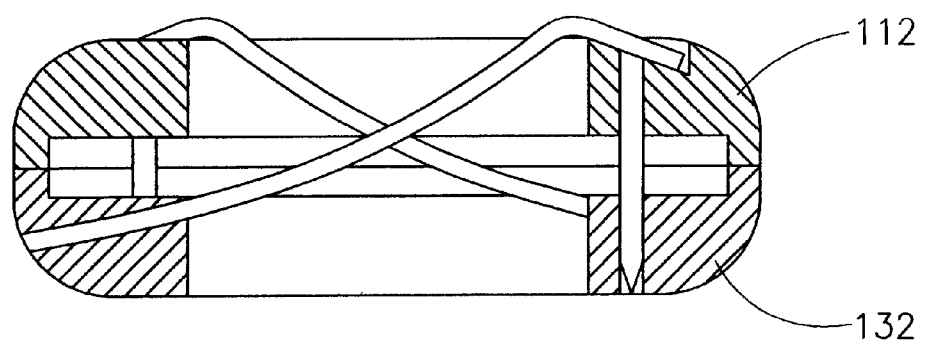
FIG. 6B is a side view of the surgical clip of FIG. 6A, taken in the direction of line VI—VI therein.

Referring now to FIGS. 6A and 6B, there is illustrated a surgical clip, referenced generally 110, according to a second embodiment of the present invention. It will be clear to those skilled in the art that, as certain portions of surgical clip 110 are similar in configuration and function to corresponding portions of surgical clip 10 (FIGS. 1–5), their description will not be repeated in the ensuing description of surgical clip 110. The clip 110 includes a first element 112 and a second element 132 which are to be fastened together, as will be discussed below. The features of first element are shown more clearly in FIGS. 7A, 7B, and 7C, and the features of second element 132 are shown more clearly in FIGS. 8A and 8B.

First element 112 comprises an elongated disk 114 having first surface 113 and second surface 115. Disk 114 has an axis of symmetry 120 which passes through end portions 116 of thereof and which passes between side portions 118 thereof. While end portions 116 and side portions 118 provide disk 114 with a closed configuration, the interior of disk 114 is provided with an opening 124, the function of which will be discussed further below. On either side of axis 120, within first surface 113, each of end portions 116 is provided with a rectangular recess.

First element 112 is preferably provided with a pair of alignment pins 126, which extend out of second surface 115. While, in the embodiment shown, pins 126 are attached to the surface 115 of disk 114 at the portion thereof just below recesses 122, it will be appreciated by persons skilled in the art that the pins 126 may be attached at any other suitable point of surface 115.

Second element 132 (FIGS. 6B, 8A, 8B) includes an elongated disk 134 having first surface 123 and second surface 125. Disk 134 has an axis of symmetry 130, which passes through end portions 136 thereof and which passes between side portions 138 thereof. End portions 136 and side portions 138 provide disk 134 with a closed configuration. Disk 134 is provided with an opening 135. A pair of clamping bars 40 is attached to end portions 136, on either side of and parallel to axis 130. Disk 134 may be fabricated from any metal or plastic material which is suitable for use in surgical procedures, such as plastic, stainless steel, or any other biocompatible material, while clamping bars 40 are fabricated from a shape memory alloy or superelastic material, such as is known in the art, which is suitable for use in surgical procedures. If desired, only the actual joint of clamping bars 40 to disk 134 may be formed of a shape memory alloy/superelastic material, while clamping bars 40 may be made from any suitable metal or plastic material.

Figure 10:
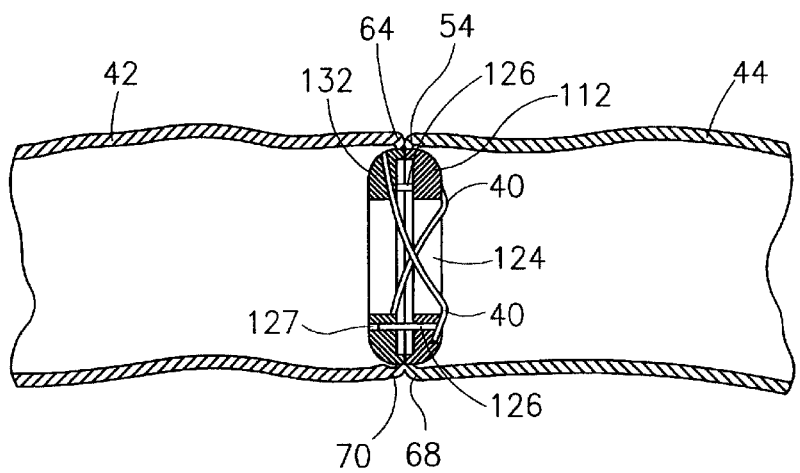
FIG. 10 is a cross-sectional view of the joined hollow organ portions shown in FIG. 9, with the surgical clip elements fastened together.

Second element 132 is preferably provided with a pair of bore holes 127, which extend from surface 125, at least partially through disk 134. The exact positioning of holes 127 is determined by the positioning of pins 126 such that, when first element 112 and second element 132 are brought together, as shown in FIGS. 6B and 10, pins 126 will be positioned within respective holes 127, thus providing clip 110 with means for maintaining alignment between elements 112 and 132.

When first element 112 and second element 132 of clip 110 are properly fastened together, clamping bars 40 of second element 132 pass through opening 124 of first element 112, sit within respective recesses 122, and press against surface 113, so as to force disks 114 and 134 to abut one another along their entire circumference. As noted above, the pins 126 and holes 127 are aligned so as to provide a means for the exact positioning of the clamping bars 40 within recesses 122.

While the surgical clip 110 according to the present invention has been shown and described as one specific embodiment, it will be appreciated by persons skilled in the art that other configurations of the clip may be achieved without departing from the scope of the invention. For example, while disks 114 and 134 are shown in the drawings as being oval and as having a periphery which is thicker in cross-section that its interior, other configurations of disks may be suitable for use in providing surgical clips according to the present invention, such as circular disks or disks having cross-sections of uniform thickness.

Figure 8A:
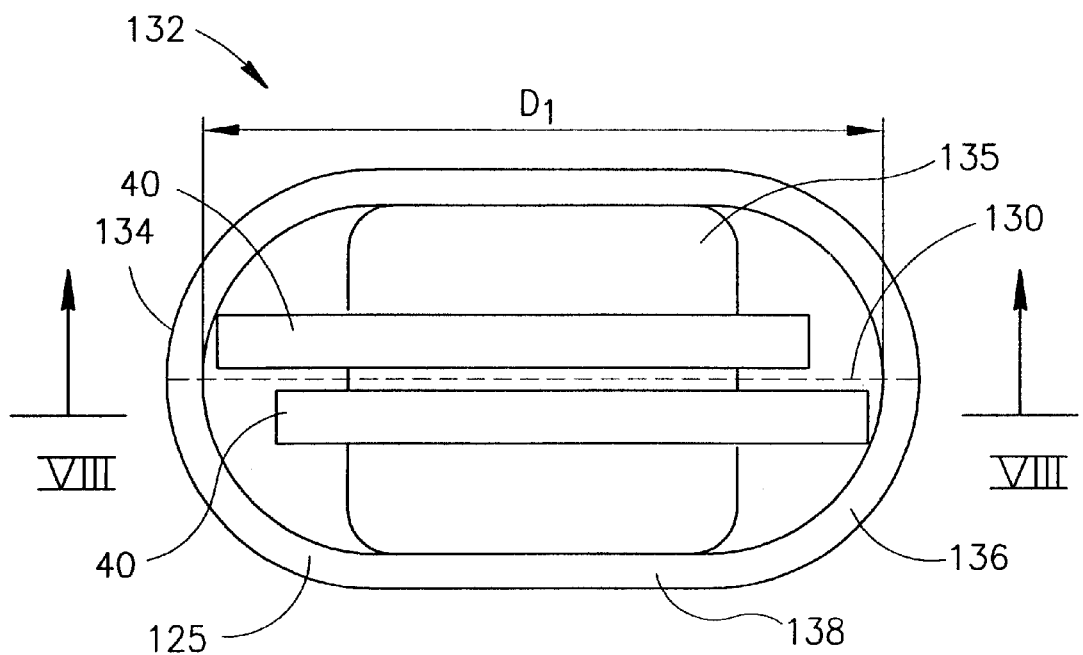
FIG. 8A is a pictorial illustration of a second element of the surgical clip of FIGS. 6A and 6B.
Figure 8B:
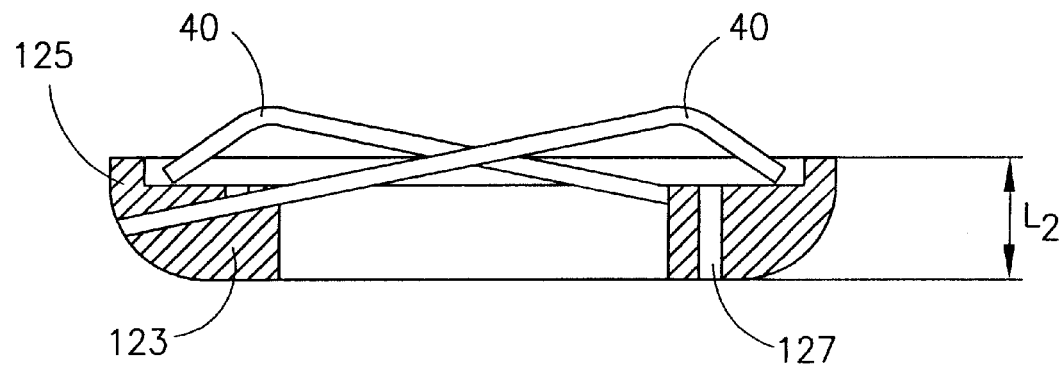
FIG. 8B is a side view of the second element of the surgical clip shown in FIG. 8A, taken along line VIII—VIII therein.

While clamping bars 40 shown in FIG. 6A and 8A are configured so as to be spaced apart, it will be appreciated by persons skilled in the art that the amount of spacing between clamping bars 40 is to be determined by the relative distance between the recesses 122 provided in first element 112 such that, when first element 112 and second element 132 are fastened together, as will be discussed below, each clamping bar 40 rests in its proper position within its respective recess 122. Also, clamping bars 40 may either be configured as straight (not shown), curved as shown in FIG. 8B, or curved as shown in FIGS. 9 and 10.

The disk 114 of first element 112 and the disk 134 of second element 132 may be fabricated from any suitable biocompatible material, such as plastic, while the alignment pins 126 and clamping bars 40 may be fabricated from metal. In this case, pins 126 may be attached to disk 112 and clamping bars 40 may be attached to disk 134 by any means known in the art, such as by inserting the metal portions into the plastic portions during production. It will be appreciated by persons skilled in the art that the description of the present invention as shown in FIGS. 6–10 relates to a second embodiment of the present invention only, which is fabricated of both plastic and metal.

Figure 9:
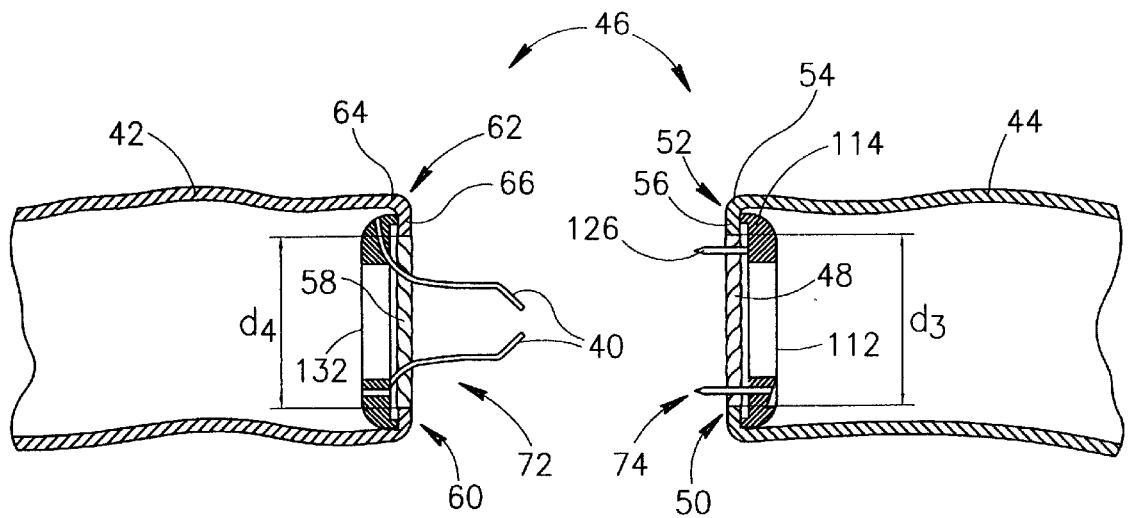
FIG. 9 is a pictorial cross-sectional illustration of first and second portions of a hollow organ, inside which there have been placed respective first surgical clip element, shown in FIGS. 7A, 7B, and 7C, arid second surgical clip element, shown in FIGS. 8A and 8B, in accordance with the second embodiment of the present invention, portions of the second element of the surgical clip being in a plastic state.

With additional reference to FIG. 9, there are shown portions 44 and 42, respectively, of a hollow organ 46, to which it is desired to provide anastomosis, as shown in FIG. 10. Organ portions 44 and 42 have respective open ends 74 and 72. The method of the present invention will now be described with reference to clip 110. However, it will be appreciated by persons skilled in the art that the method of the present invention may be carried out by utilizing any embodiment of the clip in accordance with the present invention.

Figure 7A:
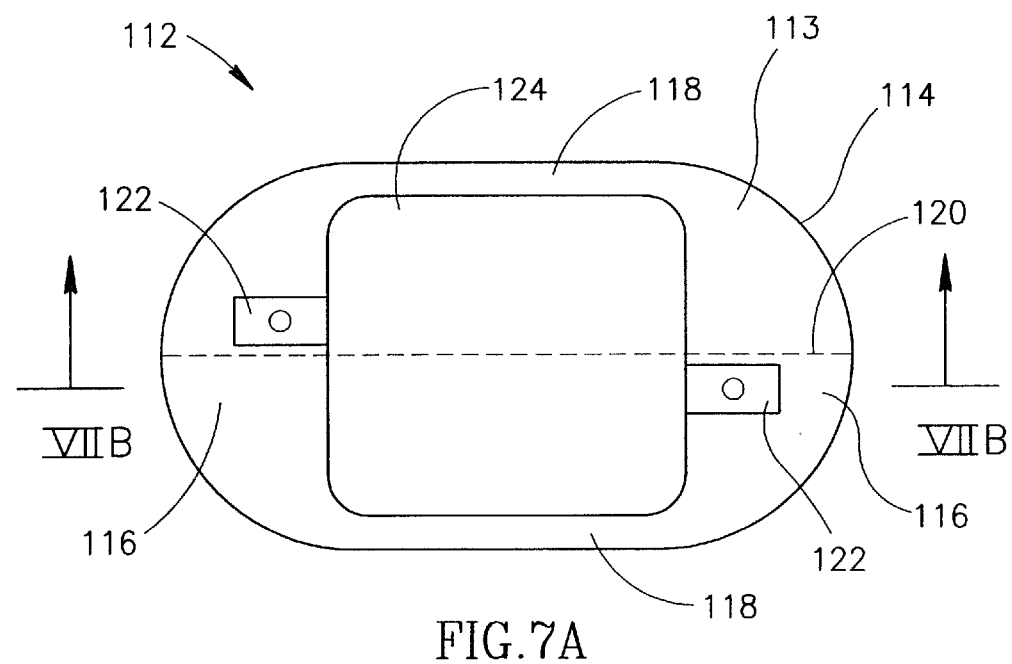
FIG. 7A is a pictorial illustration of a first element of the surgical clip of FIGS. 6A and 6B.
Figure 7B:
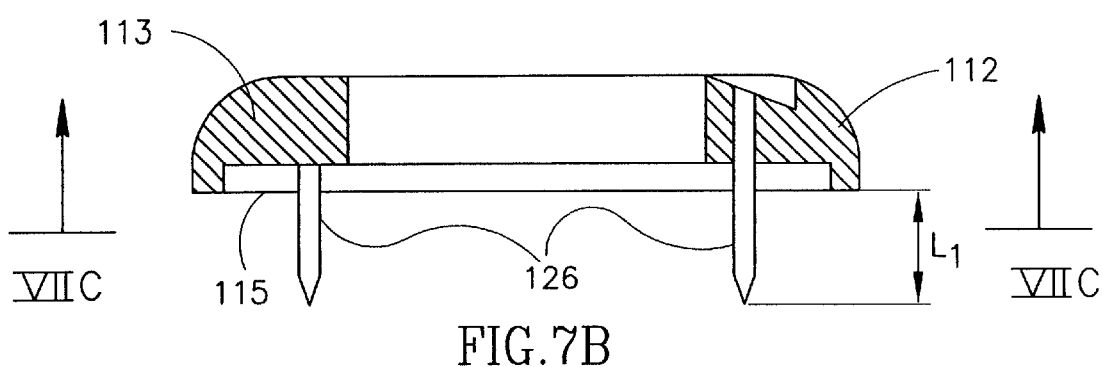
FIG. 7B is a side view of the first element of the surgical clip shown in FIG. 7A, taken along the line VIIB—VIIB therein.
Figure 7C:
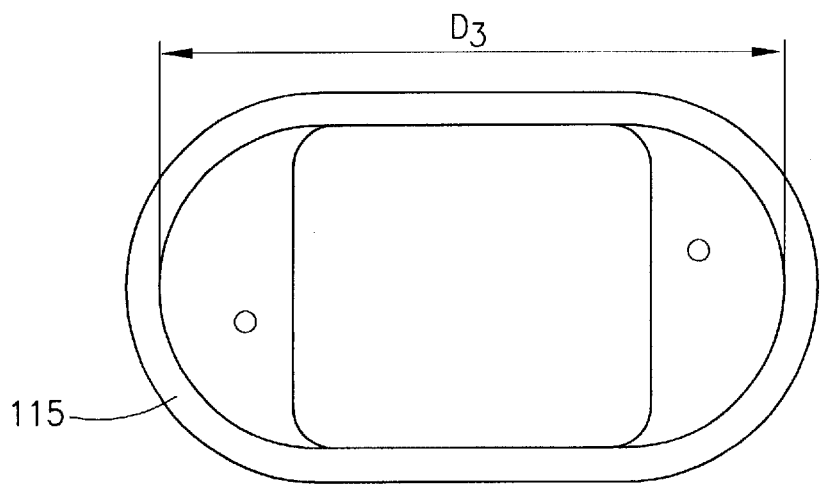
FIG. 7C is a side view of the first element of the surgical clip shown in FIG. 7B, taken along the line VIIC—VIIC therein.

A line of stitches 48, such as a line of purse string stitches, which are commonly used in surgical procedures, is surgically placed in a tissue section 50 located near the end of organ portion 44, along the periphery thereof, such that the stitches 48 pass therethrough. The stitches 48 are then gathered, by means known in the art, such that, at the location of the gathered stitches 48, the diameter $d_3$ of the cross-sectional area of organ portion 44 is reduced until it is less than the distance $D_3$ (FIG. 7C). First element 112 of clip 110 is then placed, via open end 74, inside organ portion 44, such that disk 114 is positioned along the inner surface thereof, and each of alignment pins 126 is inserted between one of stitches 48 and the inner surface of tissue section 50.

Insertion of the disk 114, as far as possible, into organ portion 44 will cause the tissue portions 54 and 56 to form a fold 52 along stitches 48, such that tissue portion 54 abuts disk 114 along its entire periphery. Organ portion 44 is then ready to be joined to organ portion 42.

As discussed above, clamping bars 40 of second element 132 of clip 110 may be fabricated either from a thermosensitive shape memory alloy or from a superelastic material. When employing a shape memory alloy, second element 132 is cooled until it reaches its lower phase transition temperature, as known in the art, the clamping bars 40 of second element 132 thus being in a plastic state. The phase transition temperature may be generally any temperature above −273° C., preferably in the range of 25–35° C., and below body temperature. Clamping bars 40 are moved apart a desired distance and second element 132 is preserved in the cooled state for as long as required until insertion into the organ portion 42. When employing a superelastic material, clamping bars 40 are moved apart a desired distance, by the use of a special instrument intended for this purpose, as discussed below.

A line of stitches 58 is surgically placed in a tissue section 60 located near the end of organ portion 42, along the periphery thereof, such that stitches 58 pass therethrough. The stitches are then gathered, by means known in the art, such that, at the location of the gathered stitches 58, the diameter $d_4$ of the cross-sectional area of organ portion 42 is reduced until it is less than the distance $D_4$ (FIG. 8A) between the side portions 138 of disk 134. Second element 132 of clip 110 is then placed, via open end 72, inside organ portion 42 such that disk 134 is positioned along the inner surface thereof, and each of clamping bars 40 is inserted between one of stitches 58 and the inner surface of tissue section 60, such that clamping bars 40 protrude out of the open end 72 of organ portion 42. Insertion of the clamping bars 40 will cause the tissue portions 64 and 66 to form a fold 62 along stitches 58, such that tissue portion 64 abuts disk 134 along its entire periphery.

As shown in FIG. 9, organ portions 42 and 44 of organ 46 are positioned adjacent one another, and are brought closer together, such that clamping bars 40 of second element 132 are inserted through opening 124 of first element 112. At the same time, alignment pins 126 are inserted into holes 127. Once they have been brought into contact, as shown in FIG. 10, tissue portion 64 of organ portion 42 abuts tissue portion 54 of organ portion 44. Clamping bars 40 are then allowed to return to their original position, relative to disk 134, either by warming of the second element 132 by the organ portion 42, when a thermosensitive shape memory alloy is utilized, or by removal of the special instrument, when a superelastic material is used, as discussed above.

When employing a thermosensitive shape memory alloy, the relative positions of organ portions 42 and 44 of organ 46 and the relative positions of first element 112 and second element 132 in relation thereto must be maintained for a period of time during which the temperature of organ 46 is effective to cause the temperature of the clamping bars 40 to rise to at least its upper phase transition temperature, which, preferably, is body temperature. During the time that the temperature of clamping bars 40 rises towards its transition temperature, disks 114 and 134 converge and press tissue portions 54 and 64 of organ portions 44 and 42 located therebetween more and more tightly against each other. The rate by which the temperature of clamping bars 40 rises may be accelerated by heating clip 110, for example, by any method known in the art. Once the temperature of clamping bars 40 has risen above the transition temperature, clamping bars 40 have returned to their elastic state, as shown in FIGS. 6A, 6B, 8A, 8B, and 10, and maintain tissue portions 54 and 64 adjacent one another.

Due to the pressure exerted by clip 110 on organ portions 44 and 42, respective tissue portions 54 and 64 are pressed so tightly against each other that blood flow to these tissue portions ceases, resulting in eventual necrosis of these tissue portions 54 and 64. As tissue portions 54 and 64 die, the tissue portions 68 and 70 immediately thereoutside mend together such that portions 42 and 44 of organ 46 are joined and organ 46 may function as one continuous organ. Once tissue portions 54 and 64 die, they, together tissue portions 56 and 66 and with clip 110, become separated from organ portions 42 and 44, and are passed out of organ 46, by the normal activity thereof. For example, if organ 46 is the small intestine, and the direction of peristalsis is from portion 42 towards portion 44, then clip 110 and tissue portions 54, 64, 56, and 66 will be passed through portion 44 by the normal activity of the small intestine.

Figure 11:
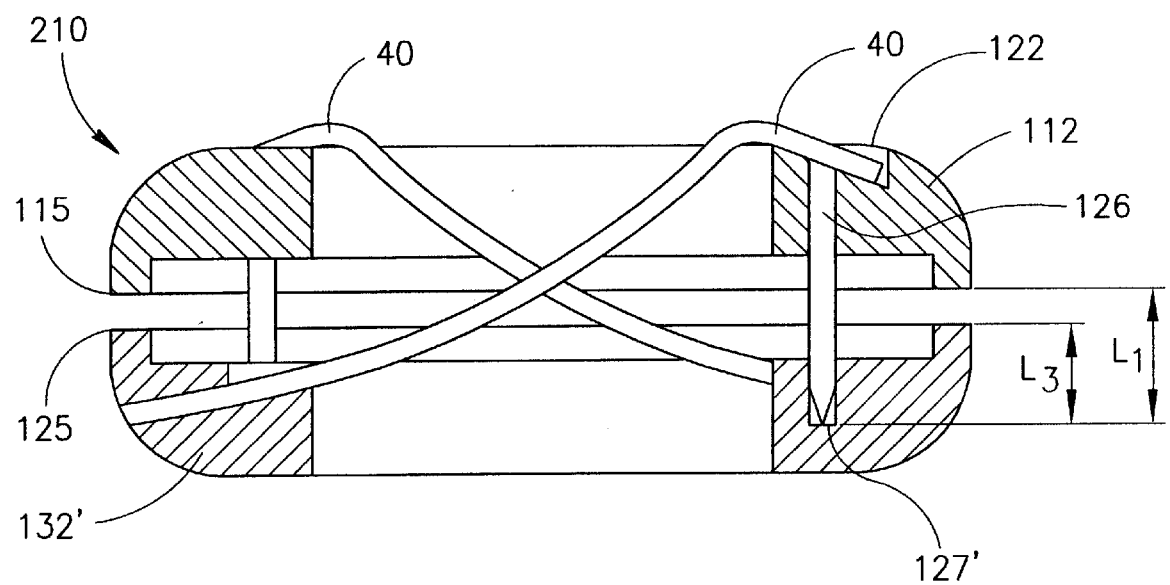
FIG. 11 is a cross-sectional view of a surgical clip, constructed in accordance with a third embodiment of the present invention.

The amount of pressure exerted by the first and second elements of a surgical clip according to the present invention on the tissue portions pressed therebetween is dependent on the relative positions of the elements when they are above their upper phase transition temperature. For example, utilization of a surgical clip, according to either of the first and second embodiments discussed hereinabove, will result in an amount of pressure exerted on the tissue portions sufficient to actually cut through the tissue such that the tissue portions 56 and 66 (FIG. 4) are sliced away from the remainder of relative organ portions 44 and 42. This is due to the fact that, at temperatures above their upper transition temperature, the first and second elements of each of clips 10 and 110 abut each other. This is clearly shown in FIGS. 1B and 6B,

With reference to FIG. 11, there is shown a cross-sectional view of a surgical clip 210, constructed in accordance with a third embodiment of the present invention. Clip 210 includes a first element 112, which is identical to first element 112, shown in FIGS. 7A, 7B, and 7C. Clip 210 also includes a second element 132', which is similar in many respects to element 132, shown in FIGS. 8A and 8B. The difference between clip 210 and clip 110 (FIGS. 6A and 6B) is due to the difference in the relationship between the length of alignment pins 126 and the length of holes 127 (in clip 210) or 127' (in clip 210). Specifically, with regard to clip 110, the length $L_1$ of the pins 126 which protrude past surface 115 (FIG. 7B) is less than or equal to the distance $L_2$ between surface 125 and the end of hole 127 in second element 132 (FIG. 8B). Thus, alignment of pins 126 within holes 127 will allow elements 112 and 132 of clip 110 to be brought together until they abut each other. In contrast, with regard to clip 210, the length $L_1$ of pins 126 which protrude past surface 115 is greater than the distance $L_3$ between surface 125 and the end of hole 127' in second element 132' (FIG. 11). Thus, alignment of pins 126 within holes 127' will allow elements 112 and 132' of clip 210 to be brought together until pins 126 abut the ends of holes 127'. This results in surfaces 115 and 125 of respective elements 112 and 132' being maintained in a spaced relationship, preferably of approximately 0.1–1.5 mm apart.

This spaced relationship between elements 112 and 132' of clip 210 enables tissue portions 64 and 54 (FIGS. 5 and 10) to be pressed together without compressing the them to such an extent that they are sliced through, as may occur with clip 110. In this manner, blood flow to tissue portions 54, 64, 56, and 66 is decreased enough such that eventual necrosis of the tissue will occur, preferably within 5 days after the clip has been properly inserted within the organ 46. As necrosis occurs, tissue portions 68 and 70 will mend together, resulting in joining together of organ portions 42 and 44, as discussed above.

It will be appreciated by persons skilled in the art that there is a direct relationship between the size and shape of the clip used in the surgical procedure described above and the size and shape of the organ whose portions are to be joined together. It is thus possible to chose to perform the procedure with a clip of a particular size and shape so as to achieve successful results.

In order to facilitate opening of the clamping bars 40 of a second element (32, 132, 132') of a surgical clip (10, 110, 210), such as before it is fastened together with a first element (12, 112), as discussed above in accordance with the present invention, the system of the present invention is provided with a surgical clip spacer 80, shown schematically in FIGS. 12A, 12B, and 12C. Spacer 80 includes first and second surfaces 82, 84, between which there is defined a third surface 86. Surfaces 82 and 84 each include a tapered portion 88 and a wider portion 90. Tapered portion 88 terminates in a tip 92. On either side of tip 92, surface 86 is provided with a groove 94, which is positioned just next to a center line 96 of surface 86.

Figure 13:
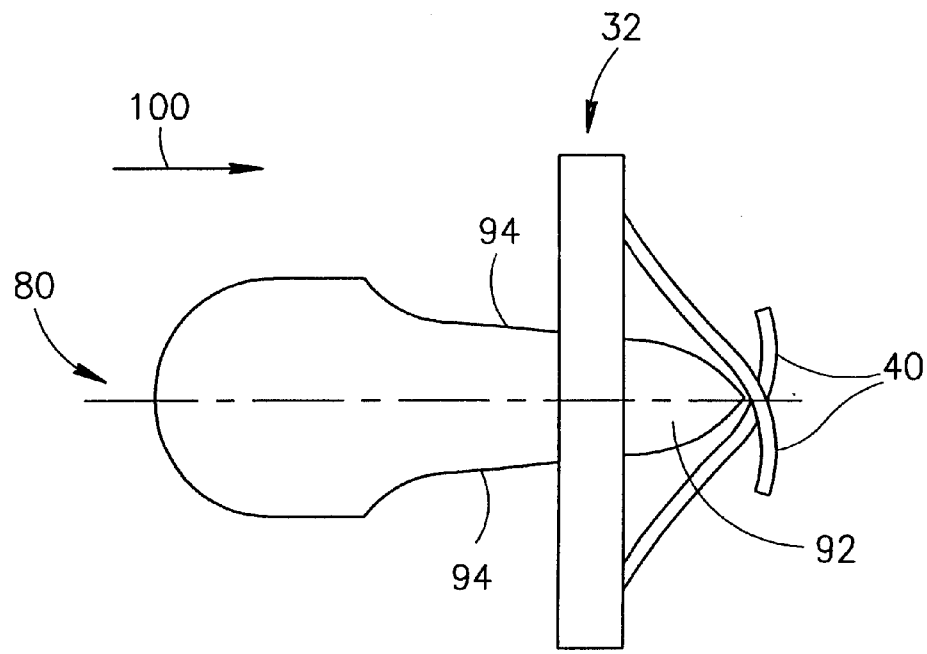
FIG. 13 is a schematic illustration of the surgical clip spacer shown in FIGS. 12A–C, and a second element of a surgical clip, in accordance with the present invention.

With reference to FIG. 13, there is described the proper use of spacer 80, as it is employed to open the clamping bars 40 of the second element of a surgical clip, for example, second element 32 of clip 10, discussed above (FIGS. 1–5). Spacer 80 is positioned such that its tip 92 contacts clamping bars 40 at the point at which they cross each other, and such that clamping bars are aligned with grooves 94. By holding second element 32 in place and by applying sufficient pressure to spacer 80 in the direction of arrow 100, clamping bars 40 are caused to separate as they slide along grooves 94, until the clamping bars 40 reach the position shown in FIG. 4.

Figure 14:
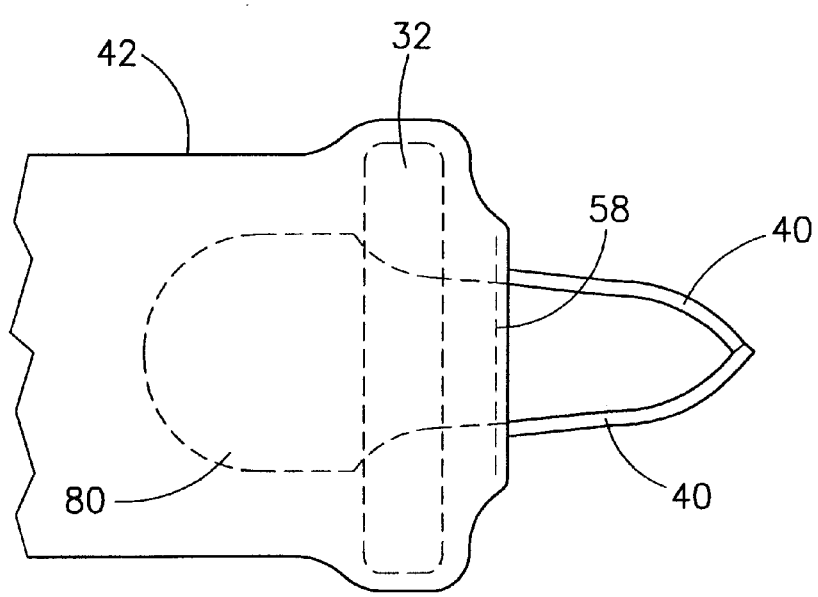
FIG. 14 is a schematic illustration of the surgical clip spacer and second element of a surgical clip shown in FIG. 13, in position within a portion of a hollow organ.

With additional reference to FIG. 14, there is discussed the proper use of spacer 80 during the surgical procedure of anastomosis, described above, with reference to FIGS. 4–5. After preparation of organ portion 44, as shown in FIG. 4, and after stitches 58 have been surgically placed in organ portion 42, spacer 80 is inserted thereinto, before insertion of second element 32. Then, second element 32 may be inserted into organ portion 42, as discussed above with reference to FIG. 4, and spacer 80 may be utilized to separate the clamping bars 40 of second element 32, as discussed above with reference to FIG. 13. Once separated, clamping bars 40 of second element 32 may be passed between support bars 22 of first element 12, as discussed above (FIG. 4). By manipulating spacer 80 through organ portion 42, second element 32 may be released therefrom, thus allowing clamping bars 40 to return to their closed configuration, resulting in first element 12 and second element 32 being fastened together. As discussed above with reference to FIG. 5, once clip 10 becomes separated from organ 46, the clip 10, together with spacer 80, is passed out of organ 46 by the normal activity thereof.

While spacer 80 is shown in FIGS. 12–14 as having a particular configuration, it will be appreciated by persons skilled in the art that the configuration shown is for illustrative purposes only. In accordance with the present invention, a spacer having any other suitable shape may be provided. Spacer 80 may be constructed of any material suitable for use in surgical procedures, such as plastic, stainless steel, or any other biocompatible material.

It will be appreciated by persons skilled in the art that the present invention is not limited by what has been shown and described hereinabove, merely by way of illustrative example. Rather, the scope of the present invention is limited solely by the claims, which follow:

What is claimed is:

1. A surgical clip system which includes a surgical clip having:
   a first clip portion including a first length of material having a closed geometrical shape having a first surface, said shape having a central axis therethrough and having a central opening therein;
   a pair of support portions associated with said first clip portion;
   a second clip portion including a second length of material having a closed geometrical shape having a second surface of substantially the same configuration and size as that of said first clip portion, said shape having a central axis therethrough; and
   a pair of fastening elements formed of a shape memory alloy, each of said fastening elements including a first end and a second end, each of said first ends being attached to said second clip portion;
   wherein, when at a first temperature or higher, said shape memory alloy is in an elastic state, such that said pair of fastening elements are maintained in a position such that they abut said support portions, and wherein, when at a second temperature or lower, below said first temperature, said shape memory alloy is in a plastic state, thereby enabling said second ends of said pair of fastening elements to be moved away from said second length of material and to be passed between said support portions such that, upon heating of said clip to at least said first temperature, said pair of fastening elements returns to said position such that they abut said support portions, thereby pressing against said pair of support portions, thereby pressing said first and second lengths of material towards each other, thereby to apply a compressive force to tissue located between said first and second lengths of material.

2. The surgical clip system according to claim 1, wherein said first clip portion, said support portions, and said second clip portion are fabricated from biocompatible material.

3. The surgical clip system according to claim 1, wherein each of said pair of support portions includes a pair of guide elements between which one of said fastening elements is positioned when in said elastic state and when said first and second lengths of material are pressed towards each other.

4. The surgical clip system according to claim 3, wherein said guide elements are fabricated from biocompatible material.

5. The surgical clip system according to claim 1, wherein said geometrical shape is an oval.

6. The surgical clip system according to claim 1, wherein upon heating of said clip to at least said first temperature, said pair of fastening elements press against said pair of support portions, thereby pressing said first and second lengths of material towards each other such that they are maintained a distance apart of approximately 0.1–1.5 mm.

7. The surgical clip system according to claim 1, wherein upon heating of said clip to at least said first temperature, said pair of fastening elements press against said pair of support portions, thereby pressing said first and second lengths of material against each other such that said first and second surfaces substantially abut each other.

8. The surgical clip system according to claim 1, said system further including spacer means for facilitating movement of said second ends of said fastening elements away from said second length of material.

9. The surgical clip system according to claim 8, said spacer means including means insertable through said second length of material of said second clip portion.

10. The surgical clip system according to claim 9, said insertable means including means for guiding movement of said fastening elements away from said second length of material.

11. The surgical clip system according to claim 8, said spacer means fabricated from biocompatible material.

12. A surgical clip system which includes a surgical clip having:
   a first clip portion including a first length of material having a closed geometrical shape having a first surface, said shape having a central axis therethrough and having a central opening therein;
   a pair of support portions associated with said first clip portion;
   a second clip portion including a second length of material having a closed geometrical shape having a second surface of substantially the same configuration and size as that of said first clip portion, said shape having a central axis therethrough; and
   a pair of fastening elements formed of a superelastic material, each of said fastening elements including a first end and a second end, each of said first ends being attached to said second clip portion;
   wherein, in the absence of, an outside force, said pair of fastening elements are maintained in a position such that they abut said support portions, and wherein, by the application of an outside force, said second ends of said pair of fastening elements are movable away from said second length of material such that they may be passed between said support portions such that, upon removal of said outside force, said pair of fastening elements returns to said position such that they abut said support portions, thereby pressing thereagainst, thereby pressing said first and second lengths of material towards each other, thereby to apply a compressive force to tissue located between said first and second lengths of material.

13. The surgical clip system according to claim 12, wherein said first clip portion, said support portions, and said second clip portion are fabricated from biocompatible material.

14. The surgical clip system according to claim 12, wherein each of said pair of support portions includes a pair of guide elements between which one of said fastening elements is positioned when in said elastic state and when said first and second lengths of material are pressed towards each other.

15. The surgical clip system according to claim 14, wherein said guide elements are fabricated from biocompatible material.

16. The surgical clip system according to claim 12, wherein said geometrical shape is an oval.

17. The surgical clip system according to claim 12, wherein upon removal of said outside force, said pair of fastening elements press against said pair of support portions, thereby pressing said first and second lengths of material towards each other such that they are maintained a distance apart of approximately 0.1–1.5 mm.

18. The surgical clip system according to claim 12, wherein upon removal of said outside force, said pair of fastening elements press against said pair of support portions, thereby pressing said first and second lengths of material against each other such that said first and second surfaces substantially abut each other.

19. The surgical clip system according to claim 12, said system further including spacer means for facilitating movement of said second ends of said fastening elements away from said second length of material.

20. The surgical clip system according to claim 19, said spacer means including means insertable through said second length of material of said second clip portion.

21. The surgical clip system according to claim 20, said insertable means including means for guiding movement of said fastening elements away from said second length of material.

22. The surgical clip system according to claim 19, said spacer means fabricated from biocompatible material.

23. A method for anastomosing an organ of a gastrointestinal tract, said method comprising the following steps:

(a) providing a surgical clip system which includes a surgical clip having:
   a first clip portion including a first length of material having a closed geometrical shape having a first surface, said shape having a central axis therethrough and having a central opening therein;
   a pair of support portions associated with said first clip portion;
   a second clip portion including a second length of material having a closed geometrical shape having a second surface of substantially the same configuration and size as that of said first clip portion, said shape having a central axis therethrough; and
   a pair of fastening elements formed of a shape memory alloy, each of said fastening elements including a first end and a second end, each of said first ends being attached to said second clip portion;
   wherein, when at a first temperature or higher, said shape memory alloy is in an elastic state, such that said pair of fastening elements are maintained in a position such that they abut said support portions, and wherein, when at a second temperature or lower, below said first temperature, said shape memory alloy is in a plastic state, thereby enabling said second ends of said pair of fastening elements to be moved away from said second length of material and to be passed between said support portions such that, upon heating of said clip to at least said first temperature, said pair of fastening elements returns to said position such that they abut said support portions, thereby pressing thereagainst, thereby pressing said first and second lengths of material towards each other, thereby to apply a compressive force to tissue located between said first and second lengths of material;

(b) cooling at least the fastening elements of the clip to a temperature below its lower phase transition temperature;

(c) moving the second ends of the fastening elements away from the second length of material;

(d) preparing open ends of first and second organ portions to be joined, such that a cross-sectional area of each organ portion is narrowed relative to the remainder thereof;

(e) inserting the first clip portion into the first organ portion, such that the first length of material abuts the inside surface of the tissue thereof, adjacent the narrowed area thereof;

(f) inserting the second clip portion into the second organ portion, such that the second length of material abuts the inside surface of the tissue thereof, adjacent the narrowed area thereof and such that the fastening elements protrude out of the open end of the second organ portion;

(g) drawing together the open ends of the first and second organ portions wherein anastomosis is desired such that they face each other, and bringing the open ends closer together such that the fastening elements protruding out of the open end of the second organ portion pass into the open end of the first organ portion, through the first length of material, and through the pair of support portions;

(h) maintaining the relative positions of the first and second portions of the gastrointestinal tract and the first and second clip portions in relation thereto, while raising the temperature of at least the fastening elements to a temperature above its upper phase transition temperature, such that the elasticity thereof causes the fastening elements to return to a position such that the fastening elements press against the pair of support portions, thereby pressing the first and second lengths of material towards each other, thereby to apply a compressive force to tissue located between the first and second lengths of material.

24. A method for anastomosing an organ of a gastrointestinal tract according to claim 23, wherein in said step (h) the temperature of at least the fastening elements is raised to a temperature above its upper phase transition temperature by the artificial application of heat.

25. A method according to claim 23, wherein the first clip portion, the support portions, and the second clip portion are fabricated from biocompatible material.

26. A method according to claim 23, wherein each of the pair of support portions includes a pair of guide elements between which one of the fastening elements is positioned when in the elastic state and when the first and second lengths of material are pressed towards each other.

27. A method according to claim 26, wherein the guide elements are fabricated from biocompatible material.

28. A method for anastomosing a gastrointestinal tract according to claim 23, wherein the geometrical shape is an oval.

29. The method according to claim 23, wherein upon heating of said clip to at least said first temperature, said pair of fastening elements press against said pair of support portions, thereby pressing said first and second lengths of material towards each other such that they are maintained a distance apart of approximately 0.1–1.5 mm.

30. The method according to claim 23, wherein upon heating of said clip to at least said first temperature, said pair of fastening elements press against said pair of support portions, thereby pressing said first and second lengths of material against each other such that said first and second surfaces substantially abut each other.

31. The method according to claim 23, wherein: said surgical clip system further includes spacer means for facilitating movement of said second ends of said fastening elements away from said second length of material; and, between said steps (e) and (f), said method includes the additional step (e1) of: inserting the spacer means into the second organ portion.

32. The method according to claim 31, wherein, between said steps (f) and (g), said method includes the additional step (f1) of inserting the spacer means through the second length of material of the second clip portion.

33. The method according to claim 32, the fastening elements being guided away from said second length of material during said step (f1).

34. The method according to claim 31, the spacer means fabricated from biocompatible material.

35. A method for anastomosing an organ of a gastrointestinal tract, said method comprising the following steps:
(a) providing a surgical clip system which includes a surgical clip having:
a first clip portion including a first length of material having a closed geometrical shape having a first surface, said shape having a central axis therethrough and having a central opening therein;
a pair of support portions associated with said first clip portion;
a second clip portion including a second length of material having a closed geometrical shape having a second surface of substantially the same configuration and size as that of said first clip portion, said shape having a central axis therethrough; and
a pair of fastening elements formed of a superelastic material, each of said fastening elements including a first end and a second end, each of said first ends being attached to said second clip portion;
wherein, in the absence of an outside force, said pair of fastening elements are maintained in a position such that they abut said support portions and wherein, by the application of an outside force, the second ends of the pair of fastening elements are moved away from said second length of material such that they are able to be passed between said support portions such that, upon removal of the outside force, the pair of fastening elements returns to the position such that they abut said support portions, thereby pressing, thereby pressing the first and second lengths of material towards each, thereby to apply a compressive force to tissue located between the first and second lengths of material;
(b) moving the second ends of the fastening elements away from the second length of material;
(c) preparing open ends of first and second organ portions to be joined, such that a cross-sectional area of each organ portion is narrowed relative to the remainder of thereof;
(d) inserting the first clip portion into the first organ portion, such that the first length of material abuts the inside surface of the tissue thereof, adjacent the narrowed area thereof;
(e) inserting the second clip portion into the second organ portion, such that the second length of material abuts the inside surface of the tissue thereof, adjacent the narrowed area thereof and such that the fastening elements protrude out of the open end of the second organ portion;
(f) drawing together the open ends of the first and second organ portions wherein anastomosis is desired such that they face each other, and bringing the open ends closer together such that the fastening elements protruding out of the open end of the second organ portion pass into the open end of the first organ portion, through the first length of material, and through the pair of support portions;
(g) maintaining the relative positions of the first and second portions of the gastrointestinal tract and the first and second clip portions in relation thereto, while removing the outside force, thereby allowing the fastening elements to return to a position such that the fastening elements press against the pair of support portions, thereby pressing the first and second lengths of material towards each other, thereby to apply a compressive force to tissue located between the first and second lengths of material.

36. A method according to claim 35, wherein the first clip portion, the support portions, and the second clip portion are fabricated from biocompatible material.

37. A method according to claim 35, wherein each of the pair of support portions includes a pair of guide elements between which one of the fastening elements is positioned when in the elastic state and when the first and second lengths of material are pressed towards each other.

38. A method according to claim 37, wherein the guide elements are fabricated from biocompatible material.

39. A method for anastomosing a gastrointestinal tract according to claim 35, wherein the geometrical shape is an oval.

40. A method for anastomosing a gastrointestinal tract according to claim 35, wherein upon removing said outside force, said pair of fastening elements press against said pair of support portions, thereby pressing said first and second lengths of material towards each other such that they are maintained a distance apart of approximately 0.1–1.5 mm.

41. A method for anastomosing a gastrointestinal tract according to claim 35, wherein upon removing said outside force, said pair of fastening elements press against said pair of support portions, thereby pressing said first and second lengths of material against each other such that said first and second surfaces substantially abut each other.

42. The method according to claim 35, wherein: said surgical clip system further includes spacer means for facilitating movement of said second ends of said fastening elements away from said second length of material; and, between said steps (d) and (e), said method includes the additional step (d1) of: inserting the spacer means into the second organ portion.

43. The method according to claim 42, wherein, between said steps (e) and (f), said method includes the additional step (e1) of inserting the spacer means through the second length of material of the second clip portion.

44. The method according to claim 43, the fastening elements being guided away from said second length of material during said step (e1).

45. The method according to claim 42, the spacer means fabricated from biocompatible material.

* * * * *